United States Patent
Lee et al.

(10) Patent No.: US 11,510,953 B2
(45) Date of Patent: Nov. 29, 2022

(54) METHOD OF TREATING T CELL LYMPHOMAS

(71) Applicant: Chen-Yu Lee, Taipei (TW)

(72) Inventors: Chen-Yu Lee, Taipei (TW); Yi-De Kuo, New Taipei (TW); Hsuan-Ching Tseng, New Taipei (TW); Yan-Chih Liao, Taipei (TW); Chin-Chuan Lo, New Taipei (TW); Juei-Yang Lo, New Taipei (TW); Fu-Lin Hsiao, New Taipei (TW); Chiu-Nai Lin, New Taipei (TW); Kun-Cheng Lin, New Taipei (TW)

(73) Assignee: Chen-Yu Lee, Taipei (TW)

( * ) Notice: Subject to any disclaimer, the term of this patent is extended or adjusted under 35 U.S.C. 154(b) by 194 days.

(21) Appl. No.: 17/019,402

(22) Filed: Sep. 14, 2020

(65) Prior Publication Data

US 2022/0080008 A1    Mar. 17, 2022

(51) Int. Cl.
| | | |
|---|---|---|
| *A61K 36/17* | (2006.01) | |
| *A61K 36/736* | (2006.01) | |
| *A61P 35/00* | (2006.01) | |
| *A61K 36/484* | (2006.01) | |
| *A61K 36/8994* | (2006.01) | |
| *A61K 36/185* | (2006.01) | |
| *A61K 36/483* | (2006.01) | |
| *A61K 33/00* | (2006.01) | |
| *A61K 36/51* | (2006.01) | |
| *A61K 36/539* | (2006.01) | |
| *A61K 36/734* | (2006.01) | |

(52) U.S. Cl.
CPC ............ *A61K 36/17* (2013.01); *A61K 36/185* (2013.01); *A61K 36/483* (2013.01); *A61K 36/484* (2013.01); *A61K 36/736* (2013.01); *A61K 36/8994* (2013.01); *A61P 35/00* (2018.01); *A61K 33/00* (2013.01); *A61K 36/51* (2013.01); *A61K 36/539* (2013.01); *A61K 36/734* (2013.01)

(58) Field of Classification Search
None
See application file for complete search history.

(56) References Cited

PUBLICATIONS

Kim, Y.-S., et al., Herb medications on angiocentric T-cell lymphoma with intra-abdominal metastasis, a case report, J. Kor. Oriental Oncology, vol. 10 No.1, 2005.*

* cited by examiner

*Primary Examiner* — H. Sarah Park
(74) *Attorney, Agent, or Firm* — Bacon & Thomas, PLLC

(57) ABSTRACT

The present invention relates to a method for treating T cell lymphomas. The method includes: administering a Chinese medicine composition to a subject in need thereof; wherein, the Chinese medicine composition is an extract of a first mixture comprising *Ephedrae herba, Armeniacae semen amarum, Coicis semen, Glycyrrhiza uralensis, Gleditsiae spina*, and *Liquidambaris fructus*.

17 Claims, No Drawings

METHOD OF TREATING T CELL LYMPHOMAS

BACKGROUND OF THE INVENTION

1. Field of the Invention

The present invention relates to a method for treating T cell lymphomas. Specifically, the present invention relates to a method for treating cutaneous T cell lymphomas.

2. Description of Related Art

Due to the potential of Chinese herbal medicine for treating cancer, traditional Chinese herbal medicine has gradually attracted attention in recent years. The principle of applying Chinese herbal medicine is based on the practice of traditional Chinese medicine theory.

The lymphatic system is responsible for the immune function of the human body. The lymphatic system includes lymphocytes, lymph vessels, lymph glands, and lymphoid organs. Lymphomas originating from lymphoid tissues can be categorized, according to the different tumor types, into Hodgkin's lymphoma and non-Hodgkin's lymphoma. In addition, the lymphocytes can be divided into B cells and T cells, so the lymphomas can be categorized into T cell lymphomas and B cell lymphomas. Among them, T cell lymphomas have a worse prognosis than B-cell lymphomas.

The most common symptoms of patients with lymphomas are swollen lymph gland, fever, night sweats, weight loss, long-term fatigue, or skin itching. Currently, the treatments for T cell lymphomas include chemotherapy, radiation therapy, monoclonal antibody therapy, hematopoietic stem cell transplantation, peripheral blood stem cell transplantation, and the like. However, it is difficult to cure T cell lymphomas, and the recurrence rate and survival rate for prognosis are not ideal. The majority of patients barely survive for more than 5 years even though the patient has received the treatment above. Therefore, there is an urgent need to provide a new medication for patients with T cell lymphomas to alleviate T cell lymphomas, improve the patient's quality of life or prolong the survival time of the patient.

SUMMARY OF THE INVENTION

The present invention relates to a composition and method for treating T cell lymphomas, which can alleviate T cell lymphomas, improve the patient's quality of life or prolong the survival time of the patient.

The present invention provides a composition for treating T-cell lymphomas, wherein the Chinese medicine composition comprises an extract of a first mixture comprising *Ephedrae herba, Armeniacae semen amarum, Coicis semen, Glycyrrhiza uralensis, Gleditsiae spina*, and *Liquidambaris fructus*.

The present invention further provides a method for treating T-cell lymphomas, comprising: administering said Chinese medicine composition to a subject in need thereof. Specifically, an effective amount of said Chinese medicine composition is administered to the subject in need thereof.

The Chinese medicine composition may be prepared by the following steps: providing the first mixture; mixing the first mixture with water to form a second mixture; heating the second mixture to obtain a crude extract; and filtering the crude extract to keep a liquid extract and obtain the Chinese medicine composition.

The first mixture of the present invention may comprise the first mixture comprises 1-4 parts by weight of *Ephedrae herba*, 3-5 parts by weight of *Armeniacae semen amarum*, 9-11 parts by weight of *Coicis semen*, 4-6 parts by weight of *Glycyrrhiza uralensis*, 7-9 parts by weight of *Gleditsiae spina*, and 9-11 pieces of *Liquidambaris fructus*.

The first mixture of the present invention may further comprise at least one ingredient selected from the group consisting of gypsum powder, *Scutellariae radix, Gentiana scabra*, and *Fructus crataegi*. In one aspect of the present invention, the first mixture may further comprise at least one ingredient selected from the group consisting of 7-11 parts by weight of gypsum powder, 2-4 parts by weight of *Scutellariae radix*, 2-4 parts by weight of *Gentiana scabra*, and 2-4 parts by weight of *Fructus crataegi*.

The first mixture of the present invention may further comprise gypsum powder. In one aspect of the present invention, the first mixture may further comprise 7-11 parts by weight of gypsum powder.

The first mixture of the present invention may further comprise *Scutellariae radix*. In one aspect of the present invention, the first mixture may further comprise 2-4 parts by weight of *Scutellariae radix*.

The first mixture of the present invention may further comprise *Gentiana scabra*. In one aspect of the present invention, the first mixture may further comprise 2-4 parts by weight of *Gentiana scabra*.

The first mixture of the present invention may further comprise *Fructus crataegi*. In one aspect of the present invention, the first mixture may further comprise 2-4 parts by weight of *Fructus crataegi*.

In the present invention, the part by weight of the first mixture may be 2.5-5 gram per part, preferably 3-4 gram per part, more preferably 3.75 gram per part, but the present invention is not limited thereto.

In the present invention, the term "treat" or "treatment" used herein refers to administer a Chinese medicine composition of the present invention to a subject in need thereof, thereby inhibiting, curing, improving, healing, ameliorating, alleviating, changing, or affecting a disease or the tendency of a disease. For instance, the method of the present invention may be used to inhibit division, replication, proliferation, invasion or transmigration of T cell lymphomas.

In the present invention, the term "effective amount" used herein refers to a necessary dose leading to expected therapeutic effects in a subject treated, and it may be changed depending on the route of administration, the use of excipients and the combined use with other medicaments.

The Chinese medicine composition of the present invention may be administered via oral administration or injection.

The Chinese medicine composition of the present invention may further comprise pharmaceutically acceptable carrier, stabilizer, thinner, dispersant, suspending agent, thickener, excipient or the combination thereof.

In the present invention, the term "acceptable" used herein means that it should be compatible with the Chinese medicine composition, preferably be able to stabilize the Chinese medicine composition, and cannot jeopardize the subject treated.

The present invention is not restrictive of the method for decocting Chinese medicine, and it can be implemented in any known manner. The present invention is not restrictive of the method for heating the Chinese medicine, and it can be implemented by any known method, such as direct heating and double-boiling.

DETAILED DESCRIPTION OF THE PREFERRED EMBODIMENT

The following embodiments are meant to explain the implementation of the present invention, they should be construed as descriptive merely, and should not restrict the remaining part of the present invention. The person having ordinary skills in the art can easily understand other advantages and effects of the present invention. The present invention may also be implemented or applied by other different embodiments, and various details in this specification may also be modified and changed according to different viewpoints and applications without departing from the spirit of the invention.

Unless specified otherwise, all technical and scientific terms described in the specification and claims of the present invention are defined as follows. In the present invention, the singular term and "the" may refer to one or more objects, unless specified otherwise. In addition, the term "comprise" is an open-ended transition word which does not limit to the items listed. The foregoing paragraphs are only systematic references and should not be construed as limitations for the subject of the invention. Unless specified otherwise, the materials used in the present invention are commercially available and easy to obtain. Possible sources for obtaining the materials are listed below and it is exemplary only.

In the following preparation examples, the part by weight is 3.75 gram per part.

Preparation Example 1

Provide 2.5 parts by weight of *Ephedrae herba*, 4 parts by weight of *Armeniacae semen amarum*, 10 parts by weight of *Coicis semen*, 5 parts by weight of *Glycyrrhiza uralensis*, 8 parts by weight of *Gleditsiae spina*, and pieces of *Liquidambaris fructus* to form a mixture; mixed with 1500 parts by weight of water; decoct the mixture for 1 hour to form a crude extract being about 400 parts by weight; filter the crude extract and collect the filtrate to obtain the extract of the present preparation example.

Preparation Example 2

The mixture of Preparation Example 1 was added with 0.5 parts by weight of *Ephedrae herba* and 8 parts by weight of gypsum powder to obtain a mixture of the present preparation example, followed by extraction in a similar manner to Preparation Example 1 in order to obtain an extract of the present preparation example.

Preparation Example 3

The mixture of Preparation Example 2 was added with 3 parts by weight of *Scutellariae radix* to obtain a mixture of the present preparation example, followed by extraction in a similar manner to Preparation Example 1 in order to obtain an extract of the present preparation example.

Preparation Example 4

The mixture of Preparation Example 2 was added with 3 parts by weight of *Gentiana scabra* to obtain a mixture of the present preparation example, followed by extraction in a similar manner to Preparation Example 1 in order to obtain an extract of the present preparation example.

Preparation Example 5

The mixture of Preparation Example 2 was added with 3 parts by weight of *Fructus crataegi* to obtain a mixture of the present preparation example, followed by extraction in a similar manner to Preparation Example 1 in order to obtain an extract of the present preparation example.

Preparation Example 6

The mixture of Preparation Example 2 was added with 2 parts by weight of gypsum powder and 3 parts by weight of *Fructus crataegi* to obtain a mixture of the present preparation example, followed by extraction in a similar manner to Preparation Example 1 in order to obtain an extract of the present preparation example.

Example 1

The patient with T cell lymphomas of Example 1 took Roaccutane as a treatment.

A treatment of the present invention applied to the patient of Example 1 was described below. A daily dose of the extract of Preparation Example 1 was administered to the patient every day, wherein the daily dose of the extract of Preparation Example 1 was divided into aliquots for ter in die administration. A follow-up report indicated that skill peeling was shown in the patient's affected area, accompanied with dryness and itchiness, and the tumor was alleviated.

Example 2

The patient with T cell lymphomas of Example 2 took Roaccutane® (Isotretinoin) as a treatment, and a photosensitive agent Methoxsalen, Zyrtec was taken during phototherapy.

A treatment of the present invention applied to the patient of Example 2 was described below. From the first day, a daily dose of the extract of Preparation Example 2 was administered to the patient every day, wherein the daily dose of the extract of Preparation Example 2 was divided into aliquots for ter in die administration. A follow-up report indicated that itchiness was not found in the patient and the tumor was alleviated.

Example 3

The patient with T cell lymphomas of Example 3 took Roaccutane® (Isotretinoin) as a treatment, and a photosensitive agent Methoxsalen, Zyrtec was taken during phototherapy.

A treatment of the present invention applied to the patient of Example 3 was described below. From the first day, a daily dose of the extract of Preparation Example 3 was administered to the patient every day, wherein the daily dose of the extract of Preparation Example 3 was divided into aliquots for ter in die administration. A follow-up report indicated that itchiness was not found in the patient, only a little pigmentation remained on the skin that has been affected, and the tumor was alleviated.

Example 4

The patient with T cell lymphomas of Example 4 took Roaccutane as a treatment, and a steroid ointment was applied externally.

A treatment of the present invention applied to the patient of Example 4 was described below. From the first day, a daily dose of the extract of Preparation Example 4 was administered to the patient every day, wherein the daily dose of the extract of Preparation Example 4 was divided into aliquots for ter in die administration. A follow-up report indicated that the patient still took the medicine as of the reporting date, and the tumor was alleviated.

Example 5

The patient with T cell lymphomas of Example 5 took Roaccutane® (Isotretinoin) as a treatment, a photosensitive agent Methoxsalen, Zyrtec was taken during phototherapy, and a steroid ointment was applied externally.

A treatment of the present invention applied to the patient of Example 5 was described below. From the first day, a daily dose of the extract of Preparation Example 5 was administered to the patient every day, wherein the daily dose of the extract of Preparation Example 5 was divided into aliquots for ter in die administration. A follow-up report indicated that the patient still took the medicine as of the reporting date, and the tumor was completely alleviated.

Example 6

The patient with T cell lymphomas of Example 6 took Roaccutane® (Isotretinoin) as a treatment, a photosensitive agent Methoxsalen, Zyrtec was taken during phototherapy, and a steroid ointment was applied externally. In addition, the patient had a rash on the right hip.

A treatment of the present invention applied to the patient of Example 6 was described below. From the first day, a daily dose of the extract of Preparation Example 6 was administered to the patient every day, wherein the daily dose of the extract of Preparation Example 6 was divided into aliquots for ter in die administration. A follow-up report indicated that the patient still took the medicine as of the reporting date, and the tumor was completely alleviated.

Although the present invention has been explained in relation to its preferred embodiment, it is to be understood that many other possible modifications and variations can be made without departing from the spirit and scope of the invention as hereinafter claimed.

What is claimed is:

1. A method for treating T cell lymphomas comprising:
    administering a Chinese medicine composition to a subject in need thereof;
    wherein, the Chinese medicine composition is an extract of a first mixture comprising 1-4 parts by weight of *Ephedrae herba*, 3-5 parts by weight of *Armeniacae semen amarum*, 9-11 parts by weight of *Coicis semen*, 4-6 parts by weight of *Glycyrrhiza uralensis*, 7-9 parts by weight of *Gleditsiae spina*, and 9-11 pieces of *Liquidambaris fructus*.

2. The method of claim 1, wherein the Chinese medicine composition is prepared by the following steps:
    providing the first mixture;
    mixing the first mixture with water to form a second mixture;
    heating the second mixture to obtain a crude extract; and
    filtering the crude extract to keep a liquid extract and obtain the Chinese medicine composition.

3. The method of claim 1, wherein the part by weight of the first mixture is 2.5-5 gram per part.

4. The method of claim 1, wherein the first mixture further comprises at least one ingredient selected from the group consisting of gypsum powder, *Scutellariae radix, Gentiana scabra*, and *Fructus crataegi*.

5. The method of claim 4, wherein the first mixture further comprises at least one ingredient selected from the group consisting of 7-11 parts by weight of gypsum powder, 2-4 parts by weight of *Scutellariae radix,* 2-4 parts by weight of *Gentiana scabra,* and 2-4 parts by weight of *Fructus Crataegi*.

6. The method of claim 5, wherein the part by weight of the first mixture is 2.5-5 gram per part.

7. The method of claim 1, wherein the first mixture further comprises gypsum powder.

8. The method of claim 7, wherein the first mixture further comprises *Scutellariae radix*.

9. The method of claim 7, wherein the first mixture further comprises *Gentiana scabra*.

10. The method of claim 7, wherein the first mixture further comprises *Fructus crataegi*.

11. The method of claim 1, wherein the first mixture further comprises 7-11 parts by weight of gypsum powder.

12. The method of claim 11, wherein the first mixture further comprises 2-4 parts by weight of *Scutellariae radix*.

13. The method of claim 11, wherein the first mixture further comprises 2-4 parts by weight of *Gentiana scabra*.

14. The method of claim 11, wherein the first mixture further comprises 2-4 parts by weight of *Fructus crataegi*.

15. The method of claim 1, wherein the method is used to inhibit division, replication, proliferation, invasion or transmigration of T cell lymphomas.

16. The method of claim 1, wherein the Chinese medicine composition is administered via oral administration or injection.

17. The method of claim 1, wherein the Chinese medicine composition further comprises a pharmaceutically acceptable carrier, stabilizer, diluent, dispersant, suspending agents, thickening agent, excipient, or the combination thereof.

* * * * *